US 6,537,758 B2

(12) United States Patent
Wahl et al.

(10) Patent No.: US 6,537,758 B2
(45) Date of Patent: *Mar. 25, 2003

(54) METHOD FOR ISOLATING NUCLEIC ACID FROM MICRONUCLEI SEPARATED FROM A CELL

(75) Inventors: Geoffrey M. Wahl, San Diego, CA (US); Noriaki Shimizu, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/951,995

(22) Filed: Sep. 13, 2001

(65) Prior Publication Data

US 2002/0102583 A1 Aug. 1, 2002

Related U.S. Application Data

(63) Continuation of application No. 09/519,931, filed on Mar. 7, 2000, now Pat. No. 6,312,908, which is a division of application No. 08/704,391, filed on Aug. 26, 1996, now Pat. No. 6,033,849, which is a continuation of application No. 08/452,275, filed on May 26, 1995, now abandoned.

(51) Int. Cl.[7] .......................... C12Q 1/68; C07H 21/04
(52) U.S. Cl. .................................... 435/6; 536/25.4
(58) Field of Search ...................... 435/6, 91.1, 91.2; 536/25.4, 25.41

(56) References Cited

U.S. PATENT DOCUMENTS

| 4,906,561 A | 3/1990 | Thornewaite | 435/6 |
| 5,427,932 A | 6/1995 | Weier et al. | 435/91.2 |
| 5,480,772 A | 1/1996 | Wangh | 435/2 |

OTHER PUBLICATIONS

Bigner, et al., *Cancer Res.*, 50, 2347–50, (1990).
Carroll, S.M., et al., "Localization of a bidirectional DNA replication origin in the native locus and in episomary amplified murine adenosine deaminase loci", *Mol. Cell. Biol.* 13, 2971–2981, (1993).
Curt, et al., *New England J. Medicine*, 308, 199–202, (1983).
Dhar et al., *Somatic Cell Molecular Genetices*, 10, 547–559, (1984).
Eckhardt, S.G., et al., "Induction of differentiation in HL60 cells by the reduction of extrachromosomally amplified c–myc", *Proc. Natl. Acad. Sci. USA* 91, 6674–6678, (Jul. 1994).
George et al., *Nucl. Acids Res.*, 12, 2731–2743, (1984).
Hahn, et al., *Genet. Anal. Tech. Appl.*, 9, 17–25, (1992).
Hayashi et al., *Mutation Res.*, 307, 245–251 (1994).
Lin, et al., "Chromasoma, 92", 11–15, (1985).
Michitch, "Isolation and Characterization of the N–MYC Gene", Ph. D. Dissertation (abstract).
Mor, et al., *Nucl. Acids Res*, 19, 117–123, (1991).
Sen, et al., *Genomics*, 19, 542–551, (1994).
Shimizu, N., et al., "Loss of amplified c–myc genes in the spontaneously differentiated HL–60 cells", *Cancer Res.* 54, 3561–3567, (1994).

(List continued on next page.)

*Primary Examiner*—Kenneth R. Horlick
(74) *Attorney, Agent, or Firm*—Schwegman, Lundberg, Woessner & Kluth, P.A.

(57) ABSTRACT

The present invention provides a method for isolating nucleic acid from micronuclei separated from a cell that involves separating micronuclei from a cell and isolating nucleic acid from the micronuclei.

23 Claims, 6 Drawing Sheets

OTHER PUBLICATIONS

Shimizu, N. et al., "Selective capture of acentric fragments by micronuclei provides a rapid method for purifying extra-chromosomally amplified DNA", *Nature Genet. 12*, 65–71, (Jan., 1996).

Tates, et al., *Mutation Res., 121*, 131–138, (1983).

Tates, et al., *Mutation Research, 74* , 11–20, (1980).

Von Hoff, D., et al., "Hydroxyureau Accelerates Loss of Extrachromosomally Amplified Genes from Tumor Cells", *Cancer Res. 51*, 6273–6279, (Dec. 1991).

Von Hoff, D.D., et al., "Elimination of extrachromosomally amplified MYC genes from human tumor cells reduces their tumorigenicity", *Proc. Natl. Acad. Sci. USA 89*, 8165–8169, (1992).

Whong, et al., *Mutation Res., 241*, 7–13, (1990).

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide for PCR of human c-myc

<400> SEQUENCE: 1
ctgggatctt ctcagcctat                                          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide for pcr of human c-myc

<400> SEQUENCE: 2
actcctctca ccatgaaggt                                          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide for pcr of beta-globin

<400> SEQUENCE: 3
gtatcatgcc tctttgcacc                                          20

<210> SEQ ID NO 4
<211> LENGTH: 20
<212> TYPE: DNA
<213> ORGANISM: Artificial Sequence -continued

```
<220> FEATURE:
<223> OTHER INFORMATION: Description of Artificial Sequence:
      oligonucleotide for pcr of beta-globin

<400> SEQUENCE: 4
aagggcctag cttggactca                                                    20
```

METHOD FOR ISOLATING NUCLEIC ACID FROM MICRONUCLEI SEPARATED FROM A CELL

This application is a continuation of U.S. application Ser. No. 09/519,931, filed Mar. 7, 2000, U.S. Pat. No. 6,312,908, which is a divisional of U.S. application Ser. No. 08/704,391, filed Aug. 26, 1996, issued on Mar. 7, 2000 as U.S. Pat. No. 6,033,849, which is a continuation of U.S. patent application Ser. No. 08/452,275, filed May 26, 1995, abandoned.

This invention was made with Government support under Grant No. CA 48405 awarded by the National Institutes of Health and Grant No. DAMD17-94-J-4359, awarded by the U.S. Army Medical Research Acquisition Activity. The Government has certain rights in this invention.

BACKGROUND OF THE INVENTION

1. Field of the Invention

This invention relates generally to gene amplification and specifically to a method for isolation of extrachromosomal amplified nucleic acid sequences.

2. Description of Related Art

Gene amplification in tumor cells results in the production of multiple copies of a genomic region. Amplification of oncogenes leads to the over expression of proteins participating in the transduction of growth-related signals and confers a growth advantage to tumor cells. Clinically, oncogene amplification is extremely common in human tumors and correlates with a poor prognosis for patients with ovarian cancer (HER-2/neu), breast cancer (c-myc, HER-2/neu), neuroblastoma (N-myc), or small cell lung cancer (c-myc) (Slamon, et al., *Science* 235:177, 1987; Slamon, et al., *Science*, 244:707, 1989; Seeger, et al., *N. Engl. J. Med.*, 313:1111, 1985; Johnson, et al., *J. Clin. Invest.*, 78:525, 1986). There is also evidence that amplification of drug resistant genes is associated with both in vitro and in vivo resistance of a patient's tumor to an antineoplastic agent (Schimke, R., *Cancer Res.*, 44:1735, 1984; Stark, G., *Cancer Surv.* 5:1, 1986; Trent, et al., *J. Clin. Oncol.*, 2:8, 1984; Curt, et al., *N. Engl. J. Med.*, 308:199, 1983).

Amplified genes have been localized to two types of cytogenetically distinguishable structures. These structures can be located on the chromosome, within homogeneously staining regions (HSRs), or they can be reside extrachromosomal either as submicroscopic elements called episomes or as larger structures called double minute chromosomes (Carroll, et al., *Mol. Cell. Biol.*, 8:1525, 1988; Von Hoff, et al., *J. Clin. Invest.*, 85:1887, 1990; Von Hoff, et al., *Proc. Natl. Acad. Sci. USA*, 85:4804, 1988). The occurrence of DMs in a malignant cell line was first described by Spriggs, et al. (*Br Med J*, 2:1431, 1962). DMs are paired, acentric fragments that segregate randomly at cell division and can be detected in the majority of primary tumors at biopsy (Benner, et al., *Anticancer Drugs*, 2:11, 1991; Gebhart, et al., *Int. J. Cancer*, 34:369, 1984). DMs tend to vary in size and also in number of DMs per cell.

Genes amplified on DMs can be lost spontaneously at each cell division or can be eliminated by treatment with hydroxyurea (HU) at concentrations that do not inhibit DNA synthesis or ribonucleotide reductase (Von Hoff, et al., *Proc. Natl Acad Sci, USA*, 89:8165, 1992; Von Hoff et al., *Cancer Res.*, 51:6273, 1991). It appears that HU-treatment of cells containing DMs results in an increase in micronuclei formation, and the capture of the DMs within the micronuclei (Von Hoff, et al., *Proc. Natl Acad Sci, USA*, 89:8165, 1992; Von Hoff, et al., *Proc. Am Assoc. Cancer Res.*, 33:359, 1992). By contrast, HSRs are not lost during cell division or by treatment with HU and represent a stable form of gene amplification. Elimination c-myc genes contained in DMs from a colon cancer cell line of neuroendocrine origin (COLO 320 DM) reduced its tumorigenicity in nude mice (Von Hoff, et al., *Proc. Natl. Acad. Sci., USA*, 89:8165, 1992). Studies have shown that treatment of HL60 cells with low concentrations of HU reduced the number of c-myc-containing DMs, which led to decreased c-myc expression and induction of differentiation (Echardt, et al., *Proc. Natl. Acad. Sci., USA*, 91:6674, 1994; Shimizu, et al., *Cancer Res.*, 54:3561, 1994). The studies also showed that agents which eliminate extrachromosomal DNA also alter tumor phenotype.

Similarly, previous studies have shown that when the selective pressure of a drug is removed from mama cells that carry unstably amplified genes on extrachromosomal particles, the cells gradually lose those amplified genes (lose their DMS or episomes). Snapka and Varshavsky previously showed that HU could increase the rate of loss of unstably amplified dihydrofolate reductase (DHFR) genes from mouse cells (*Proc. Natl. Acad. Sci., USA*, 80:7533, 1983). Von Hoff, et al., showed a similar elimination of the multi-drug resistance gene 1 (MDR1) gene in vinblastine resistant human squamous tumor cells, as well as carbamylphosphate synthetase, aspartate transcarbamylase, dihydro-orotase (CAD) genes from N-(phosphonacetyl)-L-aspartic acid (PALA) resistant Chinese hamster ovary cells, and DHFR genes from methotrexate resistant human squamous tumor cells (*Cancer Research*, 51:6273, 1991).

The persistence of DMs implies that these acentric elements express one or more genes that impart a growth or survival advantage to the cell. Identification of the expressed nucleic acid sequences contained in such DMs would provide a means for developing appropriate diagnostic, prognostic and therapeutic strategies.

SUMMARY OF THE INVENTION

The knowledge that gene amplification occurs in cancer cells provides an unparalleled opportunity for developing therapeutic approaches that are highly specific for tumor cells. The ability to eliminate amplified genes by removal or selective interference with their expression is enhanced by the determination of the identity of the amplified gene. The present invention provides a method for isolating and for identifying amplified genes which exist extrachromosomally in DMs within a cell.

The method of the invention allows isolation and molecular cloning of target nucleic acid sequences contained in extrachromosomal amplified loci. The identity of such nucleic acids or genes, whether previously known or unknown, provides a means for more accurate diagnosis and prognosis for a subject having a disorder such as a cancer. The identity of the genes also provides a method for monitoring the course of therapy for such a subject.

DETAILED DESCRIPTION OF THE INVENTION

Figure 1:
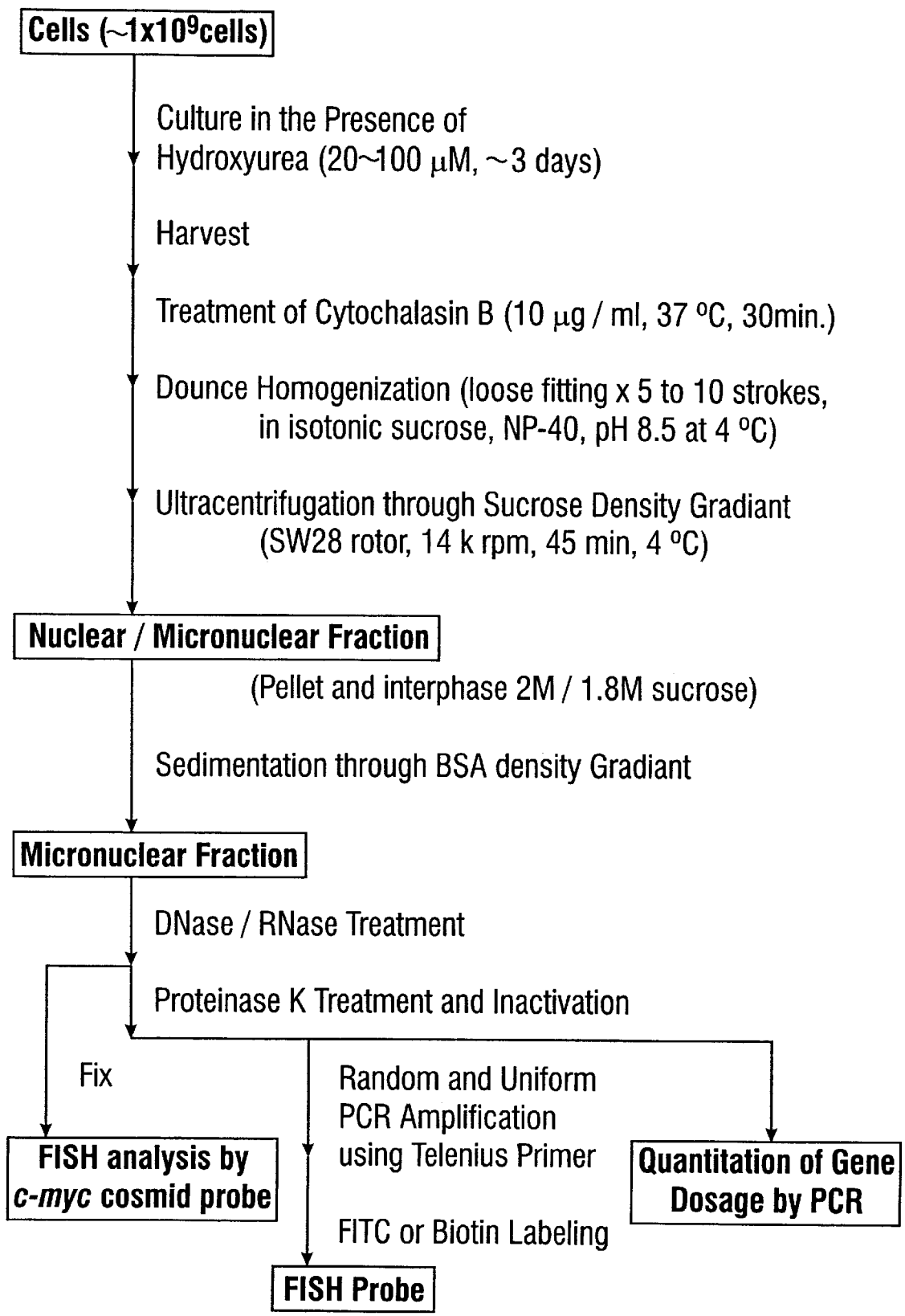
FIG. 1 shows a flow chart for isolation of micronuclei and amplified nucleic acid sequences contained within the micronuclei.

The present invention provides a method for isolating extrachromosomal amplified nucleic acid sequences from a cell having or suspected of having a cell proliferative disorder. Such disorders are associated with the amplification of cell growth control genes, oncogenes, multidrug resistance genes, and growth factor receptors, for example. The method of the invention provides a means for the identification of both previously known and of unknown expressed amplified nucleic acid sequences. Once the amplified nucleic acid is isolated and identified, probes can be developed for use in diagnosis, prognosis, and for monitoring a particular therapeutic regime.

In a preferred embodiment, the invention provides a method for isolating an amplified target nucleic acid associated with a cell proliferative disorder comprising subjecting a cell suspected of having a cell proliferative disorder to conditions sufficient to produce micronuclei, isolating the micronuclei from the cell, amplifying target nucleic acid in the micronuclei, wherein the target nucleic acid is associated with a cell proliferative disorder, and isolating the amplified target nucleic acid.

The term "isolated" as used herein refers to polynucleotides substantially free of other nucleic acids, proteins, lipids, carbohydrates or other materials with which they are naturally associated. Polynucleotide sequences of the invention include DNA, cDNA and RNA sequences which encode amplified extrachromosomal target gene or loci.

The method of the invention includes subjecting a cell suspected of having a cell proliferative disorder to conditions sufficient to produce micronuclei. Micronuclei refer to structures which preferably entrap extrachromosomal nucleic acid molecules and only infrequently contain chromosomes. In the method of the invention, a cell is subjected to an agent which induces micronuclei formation. Such agents include, but are not limited to inhibitors of DNA replication, DNA damaging agents, inhibitors of topoisomerase II, and membrane disrupting agents. Examples of such agents which induce micronuclei formation include hydroxyurea, retinoic acid, dimethyl sulfoxide, guanazole, etoposide, proflavine, and difluoromethylornithine. Other agents having the function of those described herein will be known to those of skill in the art.

Hydroxyurea is utilized in the method of the invention at a concentration of about 1 $\mu$M to 200 $\mu$M, preferably from about 50 $\mu$M to 150 $\mu$M and most preferably from about 75 $\mu$M to 100 $\mu$M. Methods for evaluating the effectiveness of agents for inducing micronuclei include preparation of metaphase chromosomes and interphase nuclei and fluorescent in situ hybridization (FISH), as described in the illustrative EXAMPLES herein.

Isolation of the micronuclei from the cell is accomplished by physical separation, density gradient separation and/or immunoseparation. Such methods will be known to those of skill in the art. Preferably, the physical separation is differential centrifugation. Density gradient separation may be utilizing a medium such as Ficoll® or Percoll® (registered trademarks of Pharmacia), sucrose, or bovine serum albumin. Other comparable density gradient separation medium will be known to those of skill in the art or will be readily ascertainable. (See for example, *Current Protocols in Molecular Biology*, Ausubel, ed., Wiley & Sons, 1994; Coligan, et al., *Current Protocols in Immunology*, Wiley Interscience, 1994).

Immunoseparation is optional and is performed by means of an antibody having the specificity of an anti-nuclear pore antibody or an anti-lamin antibody. Other antibodies having the specificity of an anti-nuclear pore antibody or an anti-lamin antibody and which bind to micronuclei are also useful in the immunoseparation process.

Following isolation of micronuclei from a cell, amplification is accomplished by polymerase chain reaction or other comparable means of amplification typically utilized by those of skill in the art. Oligonucleotide primers are used according to the invention and are employed in any amplification process that produces increased quantities of target nucleic acid or target nucleic acid sequence. Typically, one primer is complementary to the negative (−) strand of the nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target nucleotide sequence) defined by the primer which is a discrete nucleic acid duplex with termini corresponding to the ends of the specific primers employed. Those of skill in the art will know of other amplification methodologies which can also be utilized to increase the copy number of target nucleic acid.

Preferably, the method of amplifying is by PCR, as described herein and as is commonly used by those of ordinary skill in the art. Alternative methods of amplification have been described and can also be employed as long as the target nucleic acid amplified by PCR using suitable primers is similarly amplified by the alternative means. Such alternative amplification systems include self-sustained sequence replication, 3SR, which begins with a short sequence of RNA of interest and a T7 promoter. Reverse transcriptase copies the RNA into cDNA and degrades the RNA, followed by reverse transcriptase polymerizing a second strand of DNA Another nucleic acid amplification technique is nucleic acid sequence-based amplification (NASBA) which uses reverse transcription and T7 RNA polymerase and incorporates two primers to target its cycling scheme. NASBA can begin and end with either DNA or RNA and finish with either, and amplifies up to $10^8$ copies within 60 to 90 minutes. Alternatively, nucleic acid an be amplified by ligation activated transcription (LAT). LAT works from a single-stranded template with a single primer that is partially single-stranded and partially double-stranded. Amplification is initiated by ligating a cDNA to a promoter oligonucleotide and within a few hours, amplification is $10^8$ to $10^9$-fold. The Q$\beta$ replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotides, thermostable polymerase and ligase, and DNA nucleotides to geometrically amplify targeted sequences. A 2-base gap separates the oligonucleotide probes, and the RCR fills and joins the gap, mimicking normal DNA repair. Nucleic acid amplification by strand displacement activation (SDA) utilizes a short primer containing a recognition site for HincII with a short overhang on the 5' end which binds to target DNA. A DNA polymerase fills in the part of the primer opposite the overhang with sulfur-containing adenine analogs. Following amplification, HincII is added to cut the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Although PCR is the preferred method of amplification of the invention, these other methods can also be used to amplify the Amplified target nucleic acid locus as described in the method of the invention.

Primers which can be used for amplification of the target DNA sequence in the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising a suitable number of deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conducive to amplification include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers are designed to be "substantially" complementary to each strand of the nucleotide sequence to be amplified. Substantially complementary means that the primers must be sufficiently complementary to hybridize with their respective strands under conditions which allow the agent for polymerization to function. In other words, the primers should have sufficient complementarity with the flanking sequences to hybridize therewith and permit amplification of the nucleotide sequence. Preferably, the terminus of the primer that is extended has perfectly base paired complementarity with the complementary flanking strand.

Oligonucleotide primers for use in the invention may be prepared using any suitable method, such as conventional phosphotriester and phosphodiester methods or automated embodiments thereof In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Micronuclei nucleic acid amplified in accordance with the invention contains a specific known nucleic acid sequence or an unknown target nucleic acid. Thus, the nucleic acid starting materials that can be employed include, for example, DNA or RNA, including messenger RNA, wherein DNA or RNA may be single stranded or double stranded. If RNA is to be used as a template, enzymes, and/or conditions optimal for reverse transcribing the template to DNA are utilized. In addition, a DNA-RNA hybrid which contains one strand of each may also be utilized. Moreover, a mixture of nucleic acids may also be employed, or nucleic acids produced in a previous amplification reaction using the same or different primers may be utilized. The nucleic acid sequence to be amplified, may be a portion of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The agent for polymerization in the amplification reaction may be any compound or system which will function to accomplish the synthesis of primer extension products, including enzymes. Suitable enzymes for this purpose include, for example, *E. coli* DNA polymerase I, Taq polymerase, Kienow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each template strand of target nucleic acid. Generally, the amplification will be initiated at the 3' end of each primer and proceed in the 5' direction along the template strand, until synthesis terminates, producing molecules of different lengths. There may be agents for amplification, however, which initiate synthesis at the 5' end and proceed in the other direction, using the same process as described above. In any event, the method of the invention is not limited to the embodiments of amplification which are described herein.

The amplified product may be detected by analyzing it by Southern blots without using radioactive probes. In such a process, for example, a small sample of nucleic acid containing a very low level of target nucleotide sequence is amplified, and analyzed via a Southern blotting technique. The use of non-radioactive probes or labels is facilitated by the high level of the amplified signal. For determination of the identity of the isolated amplified target nucleic acid, probes which hybridize to known amplified sequences may be used first to positively identify the target sequence or to eliminate the possibility that the amplified sequence is a previously identified gene (e.g., myc, neu, PRAD, MDR1).

Nucleic acids having an amplified target sequence detected in the method of the invention can be further evaluated, cloned, sequenced, and the like, either in solution or after binding to a solid support, by any method usually applied to the analysis of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), fluorescent in situ hybridization (FISH) and the like. Molecular techniques for DNA analysis have been reviewed (Landegren, et al., *Science*, 242:229–237, 1988).

DNA sequences amplified by any one of a variety of means, can be cloned by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific nucleic acid sequence in the hybridization sample which includes a heterogeneous mixture of denatured double-stranded nucleic acid. For such screening, hybridization is preferably performed on either single-stranded nucleic acid or denatured double-stranded nucleic acid. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

The analysis of specific DNA sequences encoding amplified target nucleic acid sequences can also be obtained by: 1) isolation of double-stranded DNA sequences from the genomic DNA; 2) chemical synthesis of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., *Nucl. Acid Res.* 11:2325, 1983). One method of isolating cDNA sequences representative of the amplified target nucleic acid in the micronuclei also includes a subtractive library approach for isolating cDNA clones derived from mRNAs exhibiting higher or lower abundance.

A cDNA expression library, such as lambda gt11, can be screened indirectly for the expression product of the amplified target nucleic acid by identifying a polypeptide having at least one epitope, using antibodies specific for Amplified target nucleic acid. Such antibodies can be either polyclonally or monoclonally derived and used to detect expression product indicative of the presence of amplified target nucleic acid cDNA.

An amino acid sequence of a polypeptide can be deduced from a target nucleic acid utilizing the genetic code, however, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequence of an amplified target nucleic acid results in a functional polypeptide (at least, in the case of the sense polynucleotide strand), all degenerate nucleotide sequences are included in the invention.

There are other methods of amplification and cloning of the amplified target nucleic acid of the invention including microdissection-PCR approach which can generate PCR products for use as probes to identify phage, cosmid or YAC clones in existing libraries of normal human DNA. RNA arbitrarily primed PCR, "RAP" or "differential display" can be used to produce a DNA fingerprint of the transcribed RNA that is suitable for molecular cloning (Welsh, et al., Nucl. Acids Res., 20:4965, 1992; Liang, et al., *Science*, 257:967, 1992; Wong, et al., *Int. J. Oncol.*, 3:3, 1993, all incorporated by reference, herein).

The amplified target nucleic acid of the invention is a gene which encodes a protein such as a transcriptional regulator, a growth factor receptor, an inhibitor of the cell cycle, a G-protein, and a cell cycle-associated gene. Examples of such genes include, but are not limited to c-myc, N-myc, Her-2/neu, PRAD1, erbB-2, and H-ras. The amplified target nucleic acid may also be a gene which is referred to as a drug-resistance gene. Amplification of such genes, including dihydrofolate reductase (DHFR), carbamyl-phosphate synthetase-aspartate transcarbamylase-dihydroorotase (CAD) and multidrug resistance gene-1 (MDR1), provide a mechanism for a cell to avoid cell death upon treatment with the appropriate drug.

The method of the invention allows isolation of an amplified target nucleic acid which may be a previously known or an unknown gene. One of skill in the art will be able to use an amplification method, such as PCR, to isolate the gene for further identification. Probes which identify known genes are known and available to those of skill in the art. By elimination, one can readily determine if an amplified nucleic acid is a previously identified gene or not.

A cell proliferative disorder may be for example, associated with increased transcription and translation of an amplified target DNA sequence. The term "cell-proliferative disorder" denotes malignant as well as non-malignant cell populations which morphologically often appear to differ from the surrounding tissue. For example, the method of the invention may be usefull in diagnosing malignancies of the various organ systems, such as, for example, lung, breast, lymphoid, hematopoietic, gastrointestinal, and genito-urinary tract as well as adenocarcinomas which include malignancies such as most colon cancers, renal-cell carcinoma, prostate cancer, non-small cell carcinoma of the lung, ovarian cancer, brain cancer, uterine cancer, bladder cancer, cancer of the small intestine, and cancer of the esophagus.

The method is also useful in diagnosing non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, lipid histiocytosis, septic shock and inflammation in general. Essentially, any disorder which is etiologically linked to amplified nucleic acid target sequence would be considered a cell proliferative disorder as described herein.

The materials for use in the method of the invention are ideally suited for a kit. Such a kit comprises an agent which induces micronuclei formation, and means for amplifying target nucleic acid in the micronuclei, wherein the means comprises the necessary enzyme(s) and oligonucleotides for amplifying the target nucleic acid from a cell suspected of having a proliferative disorder.

The following examples are intended to illustrate but not limit the invention. While they are typical of those that might be used, other procedures known to those skilled in the art may alternatively be used.

EXAMPLES

Various cell lines that are known in the art to contain amplified nucleic acid sequences on extrachromosomal DMs, as well as cells suspected of having amplified nucleic acid sequences can be utilized in the method of the invention. The following illustrative examples utilized cell lines which are known to contain DMs having amplified oncogene sequences.

Example 1

Analysis of Cell Lines With DMs

Cell Lines

An early passage (passage 46) of the HL60 promyelocytic leukemia cell line was obtained from S. Colins (Fred Hutchinson Cancer Center). This cell line contains 16–32 copies of the MYC oncogene, the majority of which localize to extrachromosomal molecules ranging from 250-kbp episomes to DMs (Collins, et al., *Nature*, 270:347–349, 1977; and Von Hoff, et al., *Proc. Natl. Acad. Sci., USA*, 85:4804–4808, 1988). Passage 67 subclone 173 contains a median of 8 DMs per cell and was used for this study (Van Hoff, et al., supra; and Von Hoff et al., *J. Clin. Invest.*, 85:1887–1895, 1990). A previously described subclone of COLO 320DM (American Type Culture Collection; Quinn, et al., *Cancer Res.*, 39:4914–4924, 1979), which contains a median of 30 DMs per cell and an amplicon of 120–160 kbp (Von Hoff, et al., supra), was used. The COLO 320 HSR (HSR, homogeneously staining region) line has approximately the same number of copies of MYC dispersed at several chromosomal sites (Von Hoff, et al., supra). The NB4 neuroblastoma cell line (passage 20; kindly provided by J. Casper and V. Piaskowski, Milwaukee Children Hospital) has an ≈50-fold amplification of the NMYC gene localizing to ≈1000-kbp episomes and DMs (VanDevanter, et al., *J. Natl. Cancer Inst.*, 82:1815–1821, 1990). The SF188 glioblastoma multiform cell line, passage 220 has a 25-fold amplification of the MYC gene localizing to heterogeneously sized episomes, with a minimum size of 100 kbp, and DMs (Trent, et al., *Proc. Natl. Acad. Sci, USA*, 83:470–473, 1986).

The HL60 and COLO 320 cell lines were grown in RPMI 1640 medium with 10% fetal bovine serum (FBS), and NB4 and SF188 in RPMI 1640 medium containing 20% FBS and 2 mM glutamine. Based on previous work by Snapka and Varshavsky, *Proc. Natl. Acad. Sci., USA*, 807533–7537, 1983, HU (Squibb) was added on day 0 of culture at the concentrations indicated and was replaced each time the cells were passaged. All cells were passaged by a 1:10 dilution of confluent cultures every 3–7 days. Cell growth was determined with a hemocytometer.

Evaluation of Cells for Micronuclei and Localization of MYC Genes

Micronuclei were scored in preparations of metaphase chromosome spreads and interphase nuclei (Von Hoff et al., supra, and Naylor, et al., *Methods Enzymol.*, 151:279–292, 1987). The cells were exposed to Colcemid (0.1 µg/ml; GIBCO) for 1–3 hours, incubated in 0.075 M KCl for 20 minutes, fixed in methanol/glacial acetic acid (3:1), and dropped on wet slides. Portions of tumors that had been established in vivo were either used immediately for preparation of metaphase spreads or reestablished in cell culture to enable a comparison of the number of MYC DMs per cell under various growth conditions.

The MYC cosmid (Yuxin Yin, Salk Institute) and centromere probes (Oncor, Gaithersburg, Md.) used for in situ hybridization were labeled with biotin-16-dUTP (Boehringer Mannheim) by nick-translation with a reaction mixture containing all four dNTPs (Pharmacia). Fluorescent in situ hybridization (FISH) was conducted as described by Pinkel et al., (*Proc. Natl. Acad. Sci., USA*, 83:2934–2938, 1986).

Exposure of Cells to Hydroxyurea

All cells were continuously exposed to concentrations of hydroxyurea (Sigma) of 50, 100 and 200 µM.

Example 2

Purification of Micronuclei From Cells Containing Amplified Genes as DM and/or Episomes Cell lines Human Colo320DM or Colo320HSR neuroendocrine tumor cells (Alitalo, et al., *Proc. Natl. Acad. Sci. U.S.A.*, 80 1707–1711 (1983)) were provided by D. D. Vonhoff (University of Texas, San Antonio) and grown in RPMI1640 medium supplemented with 10% fetal calf serum. When the cell density reached $1.5 \times 10^6$ cells/ml, a subculture was made by diluting to $2.5 \times 10^5$ cells/ml with growth medium. The locations of amplified c-myc genes to DMs or HSRs were confirmed by FISH using c-myc cosmid DNA (from Yuxin Yin, Salk Institute). B-1/50 cell line (Yeung, et al., *J. Biol Chem.*, 258, 8338–8345 (1983); Nonet, et al., *Genomics* 15, 543–558 (1993)) was provided by R. Kellems (Texas Medical Center) and grown in DMEM supplemented with 1xMEM nonessential amino acids (GIBCO BRL), 15% heat-activated horse serum, 50 µM 2'-deoxycofomycin, 1.1 mM adenosine, 20 µM azaserine, and 1 mM uridine. 2'-Deoxycofomycin was obtained from the National Cancer Institute. XEW8.2.3 cell line (Carine, et al., *Somat. Cell Mol. Genet.*, 12, 479–491 (1986; Carine, et al., *Somat. Cell Mol. Genet.* 15, 445–460 (1989)) was developed by and provided from I. Scheffier (University of California, San Diego) and maintained in DMEM supplemented with 10% fetal calf serum. Human diploid WS-1 cell line was obtained from American Type Culture Collection (CRL 1502) (ATCC, Rockville, Md.) and maintained in DMEM supplemented with 10% heat activated fetal calf serum and 1×MEM nonessential amino acids. All cells were grown at 37° C. with 7% $CO_2$. Hydroxyurea (Sigma) of indicated final concentration was added to the culture when it was subcultured to lower cell density. Cells were grown in the presence of hydroxyurea for, unless otherwise noted, 3 days.

Purification of Micronuclei

This procedure was developed, in some portion, based on the protocol for the isolation of intact nuclei (Janssen, K. et al., *Current Protocols in Molecular Biology*, p4.10.1–4.10.11, John Wiley & Sons, Inc., N.Y.). FIG. 1 shows a flow chart of the isolation protocol used for isolation of micronuclei and amplified nucleic acid sequences contained within the micronuclei. The cells (~1×10$^9$ cells) were treated with 100 μM hydroxyurea for 3 days, harvested and washed twice with DMEM without serum by centrifuging 200×g for 5 min. The cell precipitate was resuspended in 20 ml of prewarmed DMEM containing cytochalasin B (10 μg/ml) and incubated for 30 min at 37° C. After collection at 200×g for 5 min, cells were resuspended in 10 ml of prechilled lysis buffer (10 mM Tris-Cl, 2 mM Mg-acetate, 3 mM $CaCl_2$, 0.32 M sucrose, 0.1 mM EDTA, 1 mM Dithiothreitol, 0.5% (v/v) Nonidet P-40, 0.15 mM spermine, 0.75 mM spermidine and 10 μg/ml cytochalasin B, pH 8.5), and Dounce homogenized (5 to 10 strokes using loose fitting pestle). The release of micronuclei from cytoplasm or nuclei was confirmed by mixing small portion of homogenate with equal volume of PBS containing 2 μg/ml of DAPI and 0.1 μg/ml of PI, and examining under fluorescence microscope using triple band path filter. Then, the homogenate was combined with the equal volume of 2M sucrose buffer (10 mM Tris-Cl, 2M sucrose, 5 mM Mg-acetate, 0.1 mM EDTA, 1 mM dithiothreitol, pH 8.0, 4° C.), and was layered onto the top of sucrose stepwise gradient (10, 5 and 5 ml of sucrose buffer containing 2 M, 1.8 M, and 1.6 M of sucrose respectively from the bottom of tube), and centrifuged in SW28 rotor, 14,000 rpm, 45 min at 4° C. After centrifugation, the pellet and the interphase between 2 and 1.8M sucrose layer, which contain nuclei and micronuclei, were recovered, and washed twice by PBS-by centrifuging 1,000×g, 20 min at 4° C. The suspension (3 ml) was then layered on the top of linear BSA gradient (0.5 to 4% in PBS, total volume 40 ml, made in 50 ml disposable syringe) (Dhar, et al., *Somat. Cell Mol. Genet.*, 10:547–559, 1984), and allowed to sit at 4° C. for 4 hours. Fractions (2 ml each) were taken from the top of gradient, diluted by PBS and centrifuged at 1,000×g for 20 min. The precipitate from fractions 1 to 8 were suspended in PBS, mixed and re-fractioned by the BSA gradient sedimentation as above. Small portion of each fraction was stained with DAPI and examined under fluorescence microscope. About 90% of DAPI positive particles present in fractions 1 to 4 were shown to typical micronuclei based on the size, the shape and the property of DAPI staining. Fractions 1 to 4 were pooled and treated with DNase I(5 μg/ml) and RNase A (40 μg/ml) for 30 min at 37° C. This fraction was determined to be purified micronuclei thereafter. A portion of purified micronuclei was fixed by methanol/acetic acid (3/1), and examined by in situ hybrization using c-myc cosmid probe. Remaining samples were treated with proteinase K (60 μg/ml) and 0.05% triton X-100 for 60 min at 50% followed by the inactivation of the enzyme at 94° C. for 12 min, and used for the gene quantitation by PCR or the generation of FISH probe.

Gene Quantitation by PCR

The amount of c-myc gene amplified on DMs in Colo320DM cells was quantitated and control β-globin gene, single copy on chromosome 11, by competitive PCR procedure as described (Siebert, et al., *BioTechniques*, 14, 244–249, 1993; Forster, et al., *BioTechniques*, 16, 1006–1008, 1994). The sequences of primers used for c-myc gene were myc-C, 5'd(CTG GGA TCT TCT CAG CCT AT)3' (SEQ ID NO:1) and myc-D, 5'd(ACT CCT CTC ACC ATG AAG GT)3' (SEQ ID NO:2). The sequences of primers used for β-globin were IVS-I, 5'd (GTA TCA TGC CTC TTT GCA CC)3' (SEQ ID NO:3), and IVS-L, 5' d(AAG GGC CTA GCT TGG ACT CA) (SEQ ID NO:4). The primer set of myc-C and myc-D amplifies 400 bp product from human c-myc gene intron 2, and the primer set of IVS-I and IVS-L amplifies 214 bp product form human β-globin gene intron 2. Internal standards for each genes were prepared by PCR amplification using c-myc or β-globin primer pairs from salmon DNA or *Saccharomyces pombe* DNA, respectively. At that time, annealing temperature was lowered to 42 C or 47° C. for c-myc and β-globin, respectively. The products were separated by agarose gel electrophoresis, and the bands of ca. 200 bp or ca. 400 bp for c-myc or β-globin, respectively, were excised. Standard DNAs in the excised bands were further purified by successive 3 rounds of PCR amplification at higher annealing temperature (63° C.) and fractionation by agarose gel electrophoresis. The amount of final PCR products, each which gave single band in agarose gel electrophoresis, were quantitated by the intensities of the ethidium bromide-stained bands in agarose gel, and used as the standard DNA for the quantitation of test DNA.

For this purpose, a series of PCR reactions were made containing equal amount of test DNA and serial 2-fold diluted standard DNA. Each tube (10 μl) contain 1×Taq buffer (Invitrogen; N for c-myc, J for β-globin), 0.2 mM each of dNTP, 20 ng each of primers, 0.2 μl of test DNA, serially diluted known amount of standard DNA, and 0.4 u of Taq polymerase (Boehringer Manheim). The tubes were heated to 95° C. for 3 min followed by 40 cycles at 94° C. for 1 min, 63° C. for 1 min, 72° C. for 2 min. After the end of PCR, the products were seperated by agarose gel electphoresis, stained with ethidium bromide and the intensities of the products from test and standard DNA, differing in the size, were compared and evaluated.

The Generation of FISH Probe from Purified Micronuclei

DNA in the proteinase K-treated micronuclei preparation was uniformly amplified by randomly primed PCR as reported by Telenius, et al. (Telenius, et al., *Genes Chrom. Cancer*, 4, 257–263, 1992) Briefly, an initial 8 cycles of PCR (94° C. for 1 min, 30° C. for 4 min, 37° C. for 2.5 min) was conducted in 5 μl of 1×Sequenase reaction buffer (USB), 0.2 mM each dNTP, and 10 μM of Telenius primer by adding 0.2 u of Sequenase (Ver. 2.0 USB) at each cycle. After this step, a conventional PCR was performed in the same tube by adding 50 μl of reaction mixture containing 1×Taq buffer B (Invitrogen), 0.2 mM each of dNTP, 2 μM of Telenius primer, 2.5 u of Taq DNA polymerase (Boehringer Mannheim). The reaction was heated to 95° C. for 3 min followed by 35 cycles at 94° C. for 1 min, 56° C. for 1 min, and 72° C. for 2 min. Amplified products were FITC-labeled by "Prime-it Fluor Fluorescence labeling kit" (Stratagene) primed with Telenius primer instead with random hexa-nucleotides supplied in the kit. In some experiments, uniformly amplified products were labeled by biotin using "BioPrime DNA System" (Life Technologies) as per the manufacturer's protocol.

Fish

Metaphase spreads were prepared as described and treated with RNase (100 μg/ml in 2×SSC, 37° C., 60 min.) Hybridization of the FISH probes was as described (Pinkel, et al., *Proc. Natl. Acad Sci., USA*, 83:2934–2938, 1986). Briefly, for each hybridization, 50~100 ng of probe was used in 15 µl hybridization mixture (containing 50% formamide, 10% dextran sulfate, 2×SSC, 6 µg salmon sperm DNA, and 3 µg human or mouse COT IDNA (BRL) depending on the probe species used) which was denatured at 75° C. for 5 min followed by 42° C., 30 min. The slides with metaphase spreads was denatured in 70% formamide, 2×SSC at 70~72° C. for 2 min, rinsed in ice cold 70%, 85% and 100% ethanol for 3 min each, and air dried. The hybridization with probes was done at 37° C. in a moist chamber overnight. The slide was then washed three times in 50% formamide, 2×SSC at 45° C. for 3 min each, three times in 2×SSC at 45° C. for 3 min each, and one time in 0.1×SSC at 60° C. for 10 min. The slide was viewed at this point when FITC labeled probes were used. Alternatively, the hybridization signal of biotin labeled probe was detected with one layer of FITC-conjugated avidin (Vector) and amplified with biotinylated anti-avidin (Vector) and a second layer of FITC-conjugated avidin. The slide was counter stained with 0.5 µg/ml of propidium iodide in Vectashield (Vector) and was examined with a Zeiss fluorescence microscope equipped with appropriate epifluorescence filters.

Figure 2A:
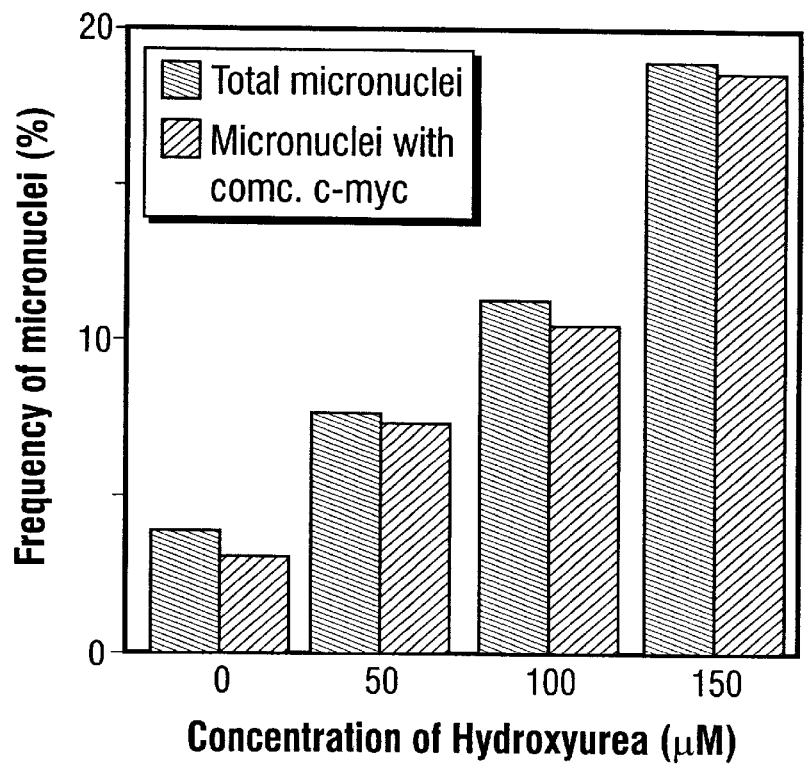
FIG. 2a shows the frequency of micronuclei having c-myc versus the total number of interphase nuclei in COLO 320DM cells.
Figure 2B:
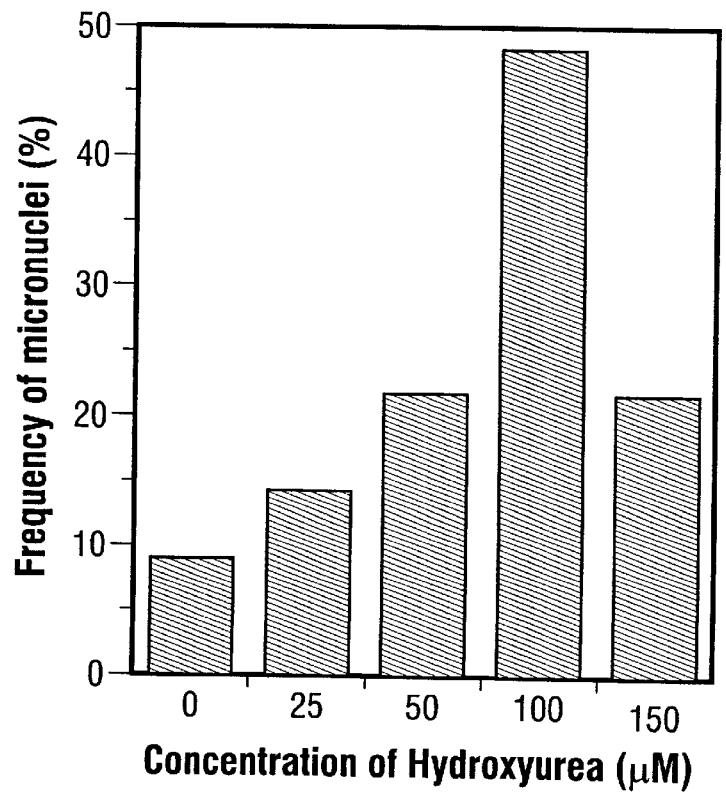
FIG. 2b shows the frequency of micronuclei in interphase nuclei in B-1/50 cells (mouse cells having amplification of adenosine deaminase gene).
Figure 2C:
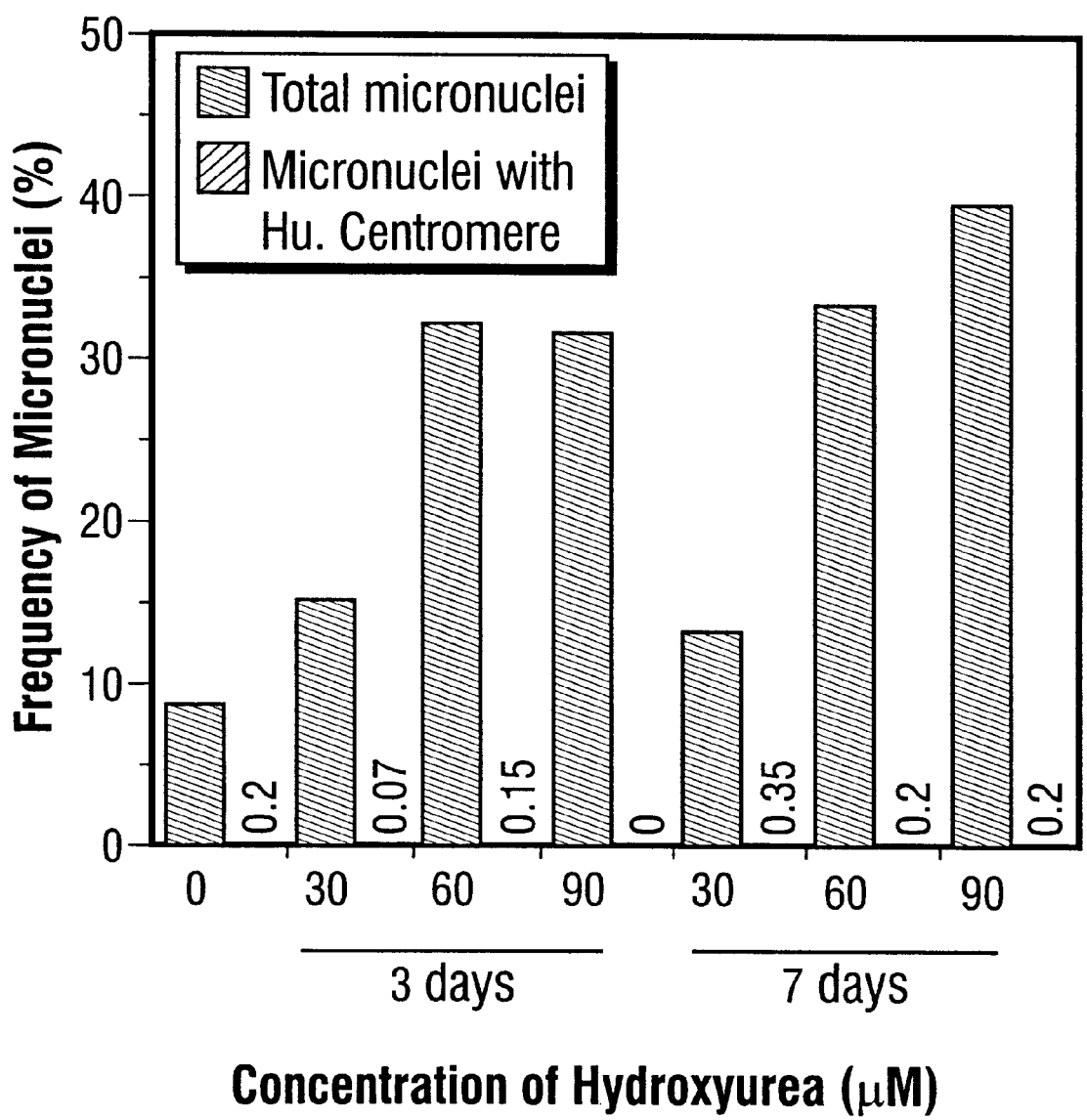
FIG. 2c shows the frequency of micronuclei in interphase nuclei in XEW 8.2.3 cells (CHO cells having human centromere sequences and minichromosome).
Figure 3:
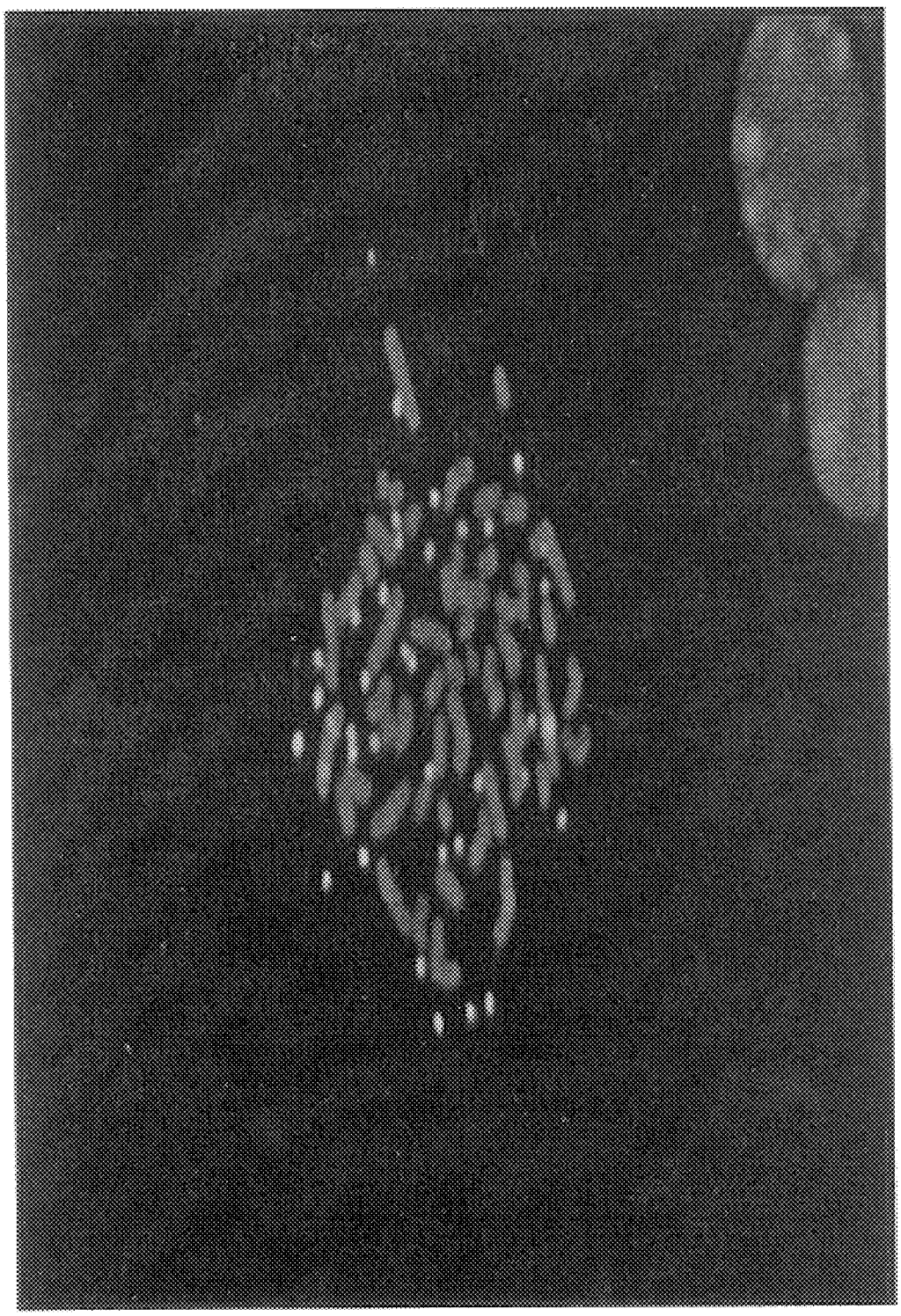
FIG. 3 shows DNA in purified micronuclei from COLO 320DM cells (FITC labeled) and FISH hybridized to COLO 320DM metaphase spreads (×1000 magnification).

The results of the FISH studies confirmed the isolation of micronuclei and DMs by the method described herein. FIG. 2a shows the frequency of micronuclei having c-myc versus the total number of interphase nuclei in COLO 320DM cells. FIG. 2b shows the frequency of micronuclei in interphase nuclei in B-1/50 cells (mouse cells having amplification of adenosine deaminase gene). FIG. 2c shows the frequency of micronuclei in interphase nuclei in XEW 8.2.3 cells (CHO cells having human centromere sequences and minichromosome). FIG. 3 shows DNA in purified micronuclei from COLO 320DM cells (FITC labeled) and FISH hybridized to COLO 320DM metaphase spreads (×1000 magnification).

Figure 4:
FIG. 4 shows micronuclei formed in COLO 320DM cells and FISH hybridized to c-myc cosmid DNA and detected by FITC (×1000 magnification).
Figure 5:
FIG. 5 shows purified micronuclei from COLO 320DM cells treated with HU (100 uM) for 3 days and FISH hybridized to c-myc cosmid DNA (×400 magnification).

FIG. 4 shows micronuclei formed in COLO 320DM cells and FISH hybridized to c-myc cosmid DNA and detected by FITC (×1000 magnification). FIG. 5 shows purified micronuclei from COLO 320DM cells treated with HU (100 uM) for 3 days and FISH hybridized to c-myc cosmid DNA (×400 magnification).

Although the invention has been described with reference to the presently preferred embodiment, it should be understood that various modifications can be made without departing from the spirit of the invention. Accordingly, the invention is limited only by the following claims.

What is claimed is:

1. A method for isolating nucleic acid from micronuclei separated from a cell comprising:
   separating the micronuclei from the cell; and
   isolating the nucleic acid from the micronuclei.

2. The method of claim 1, wherein the cell is subjected to an agent which induces formation of micronuclei in the cell.

3. The method of claim 2, wherein the agent is selected from the group consisting of an inhibitor of DNA replication, a DNA damaging agent, an inhibitor of topoisomerase II, and a membrane disrupting agent.

4. The method of claim 2, wherein the agent is hydroxyurea.

5. The method of claim 1, wherein the micronuclei are separated by physical separation, density gradient separation, immunoseparation or any combination thereof followed by treatment of the micronuclei with a nuclease.

6. The method of claim 5, wherein the physical separation is differential centrifugation.

7. The method of claim 5, wherein the immunoseparation is by means of an antibody that binds to a nuclear pore.

8. The method of claim 1, wherein the nucleic acid is a gene which encodes a protein selected from the group consisting of a transcriptional regulator, a growth factor receptor, an inhibitor of the cell cycle, a G-protein, an oncogene and a cell cycle-associated gene.

9. The method of claim 8, wherein the nucleic acid is a gene selected from the group consisting of c-myc, N-myc, Her-2/neu, PRAD1 erbB-2 and H-ras.

10. The method of claim 8, wherein the nucleic acid is a drug-resistance gene.

11. The method of claim 10, wherein the drug resistance gene is selected from the group consisting of dihydrofolate reductase (DHFR), carbamylphosphate synthetase-aspartate transcarbamylase-dihydroorotase (CAD) and multidrug resistance gene-1 (MDR1).

12. The method of claim 1, wherein the cell is derived from a tissue selected from the group consisting of lung, breast, colon, ovary, blood, brain, bladder, and uterus.

13. The method of claim 1, further comprising selectively amplifying the nucleic acid through use of an amplification process.

14. The method of claim 13, wherein the amplification process is selected from the group consisting of polymerase chain reaction, self-sustained sequence replication, nucleic acid sequence-based amplification, ligation activated transcription, Qβ replicase system, Ligase chain reaction, repair chain reaction and strand displacement activation.

15. The method of claim 1, wherein the nucleic acid is associated with a cell proliferative disorder.

16. The method of claim 1, further comprising identifying the nucleic acid contained in the micronuclei isolated from the cell by using an identification process.

17. The method of claim 16, wherein the identification process is selected from the group consisting of nucleic acid sequencing, nucleic acid hybridization, fluorescent in situ hybridization, oligomer hybridization, allele-specific oligonucleotide probe analysis and oligonucleotide ligation assays.

18. The method of claim 16, wherein the identifying is done for diagnosis, prognosis, or monitoring a therapeutic regime.

19. The method of claim 16, wherein the identifying is done for diagnosing malignancy of an organ.

20. The method of claim 19, wherein the organ is selected from the group consisting of lung, breast, lymphoid, hematopoietic, gastrointestinal and genito-urinary tract.

21. The method of claim 19, wherein the malignancy is selected from the group consisting of colon cancer, renal-cell carcinoma, prostate cancer, non-small cell carcinoma of the lung, ovarian cancer, brain cancer, uterine cancer, bladder cancer, cancer of the small-intestine and cancer of the esophagus.

22. The method of claim 16, wherein the identifying is done to diagnose a cell-proliferative disease.

23. The method of claim 22, where in the cell-proliferative disease is selected from the group consisting of psoriasis, pemphigus vulgaris, Behcet's syndrome, acute respiratory distress syndrome, ischemic heart disease, post-dialysis syndrome, leukemia, rheumatoid arthritis, acquired immune deficiency syndrome, vasculitis, lipid histiocytosis, septic shock and inflammation.

* * * * *